United States Patent [19]

LeVeen et al.

[11] 4,448,195

[45] May 15, 1984

[54] REINFORCED BALLOON CATHETER

[76] Inventors: Harry H. LeVeen, 321 Confederate Cir., Charleston, S.C. 29407; Eric G. LeVeen, 3-3 Woodlake Rd., Albany, N.Y. 12203; Robert F. LeVeen, 312 Lombard St., Philadelphia, Pa. 19147

[21] Appl. No.: 261,810

[22] Filed: May 8, 1981

[51] Int. Cl.³ .......................................... A61M 29/02
[52] U.S. Cl. ................................. 128/344; 128/348.1; 604/100; 604/103; 604/282
[58] Field of Search ................. 128/344, 348, 349 B, 128/348.1, 303.11, 303.12, 325, 658; 604/164, 170, 280, 282, 96–103

[56] References Cited

U.S. PATENT DOCUMENTS

| 3,426,744 | 2/1969 | Ball | 128/344 X |
|---|---|---|---|
| 3,435,826 | 4/1969 | Fogarty | 128/348.1 |
| 3,485,234 | 12/1969 | Stevens | 604/282 |
| 3,585,983 | 6/1971 | Kantrowitz et al. | 128/344 X |
| 3,598,126 | 8/1971 | Hoeltzerbein | 128/348 |
| 3,924,632 | 12/1975 | Cook | 604/282 |
| 3,978,863 | 9/1976 | Fettel et al. | 128/348 |
| 4,003,382 | 1/1977 | Dyke | 128/349 B |
| 4,254,774 | 3/1981 | Boretos | 128/348 |
| 4,261,339 | 4/1981 | Hanson et al. | 128/344 |
| 4,292,974 | 10/1981 | Fogarty et al. | 604/98 X |
| 4,299,226 | 11/1981 | Banka | 128/325 X |
| 4,315,512 | 2/1982 | Fogarty | 128/344 |
| 4,327,709 | 5/1982 | Hanson | 128/344 X |
| 4,362,150 | 12/1982 | Lombardi, Jr. | 604/99 X |

FOREIGN PATENT DOCUMENTS 512456 9/1939 United Kingdom ............... 128/344

Primary Examiner—Lee S. Cohen
Attorney, Agent, or Firm—Gipple & Hale

[57] ABSTRACT

A balloon catheter is formed by blow molding an elongated polyurethane tube so that one section of the tube has a thinned cross sectional balloon area between the distal end of tube which is sealed and its open proximal end. The balloon portion which is positioned adjacent the distal end has a thinner cross sectional area which allows a balloon to be formed if a fluid is introduced into the catheter by a syringe apparatus which is adapted to be attached to the lumen by a connection adaptor. A wire guide member is adapted to be inserted through the lumen for stretching the catheter when it is inserted into a blood vessel to stiffen the catheter and position it in a proper position. The wire guide member may also be mitred at predetermined intervals to determine the position of the catheter within the blood vessel.

7 Claims, 6 Drawing Figures

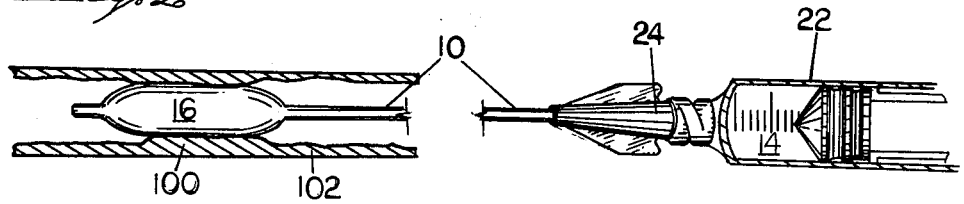
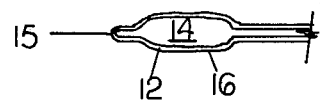
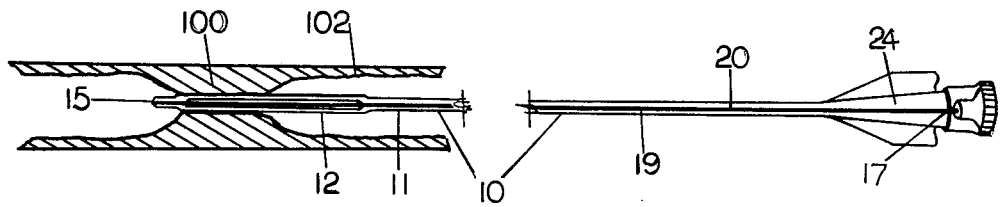
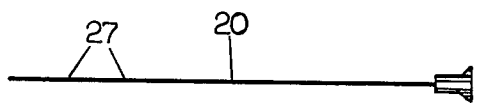
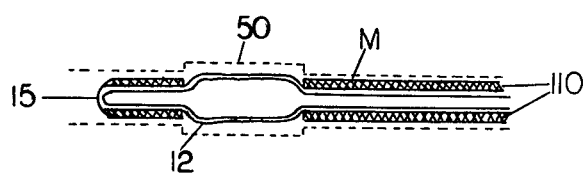
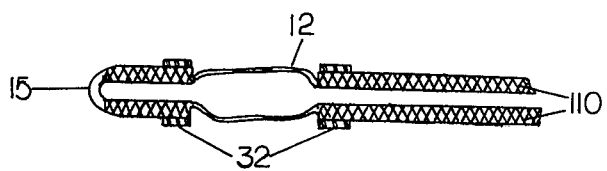

REINFORCED BALLOON CATHETER

DESCRIPTION OF THE PRIOR ART

Blood vessels and other tubular structures often undergo narrowing and obstruction. These vessels and tubular structures can be restored to their original diameter with some means of dilation. Various types of balloon catheters have been used for such dilating processes and are disclosed by many articles and patent references. U.S. Pat. No. 3,896,815 discloses a multisectional sealed balloon catheter with a guide wire which is radio opaque. The catheter balloon can be formed by expanding a distal tube portion of the catheter during the manufacturing process. The prestretching operation renders this portion of the catheter less resistant to expansion than is the unextended remainder of the catheter.

U.S. Pat. No. 4,177,815 discloses an open ended urinary balloon catheter for drainage in which a balloon is attached to a reduced diameter portion of the catheter. The narrow portion of the catheter plus the thickness of the balloon surface is not greater than the normal diameter of the catheter so that the uninflated balloon does not present a special obstacle to the insertion of the catheter through close fitting passages.

U.S. Pat. No. 3,978,863 discloses a balloon-tipped catheter with a radio opaque position indicator means. A guide wire with enlarged end beads forms the radio opaque position indicator. Thus, the position of the catheter may be determined by X-ray techniques before the wire is removed and the balloon is inflated.

In addition, the following U.S. Pat. Nos. 4,140,119; 4,149,539; and 4,188,954 generally relate to balloon-type catheters which are of interest.

SUMMARY OF THE INVENTION

The present invention pertains to balloon catheters and more specifically relates to a one piece sealed polyurethane catheter with an inflatable balloon tip. This balloon tip may be inflated when placed within the occlusion of an artery or vein to dilate the vessel to form a clear path therethrough. The catheter and balloon are a one piece unit with the balloon being a thin catheter wall portion of exact shape and size. The catheter may be formed by blow molding tubing with a fibrous reinforcement of woven glass or fine fibers of other materials. The woven fiber structure is placed over a polyurethane extruded plastic tubing which is heated and the blown outward into a mold. The molded polyurethane is then fused with the reinforcement fiber during this procedure. Alternately the balloon can be formed by stretching a section of the polyurethane tubing along the longitudinal axis of the tubing while it is in a molten state.

A guide wire is placed within the catheter to stiffen the tubing and provide guidance to the occlusion site. The guide wire stretches the balloon section lengthwise in order to reduce the diameter of the balloon section so that it can be introduced through an area of obstruction. The wire can be X-ray opaque and can be mitred by notching the wire at set intervals to measure distances on X-ray images. The catheter can be marked with opaque material or inflated with such material so that its location within the body can be ascertained through X-ray techniques. The tubing can also be banded with a steel collar at the beginning and end of the thinned section to indicate the parameters of the balloon.

In an alternative embodiment, braided shell wire reinforcement rather than the aforementioned glass fiber is used, with the braids being placed at the beginning and endings of the thinned portion but not at its center. This is to reinforce the tubing onto the thinned portion.

The above-mentioned purposes and operations of the invention are more readily apparent when read in conjunction with the following description of the drawings and the detailed description of the preferred embodiment of the present invention.

BRIEF DESCRIPTION OF THE DRAWINGS

FIG. 1 is an exploded view partially in cross-section of the inventive balloon catheter apparatus inserted into a blood vessel before expansion of the balloon portion of the catheter;

FIG. 2 is a exploded cross-sectional view of the inventive apparatus as shown in FIG. 1 with a syringe attached and fluid inserted into the balloon portion of the catheter;

FIG. 3 is a cross-sectional view of the inflated balloon catheter portion shown in FIG. 2;

FIG. 4 is a side view of a guide wire member which is used in the balloon catheter during insertion;

FIG. 5 is an enlarged cross-sectional view of the balloon catheter with wire outer braids along the tubing sections adjacent the balloon portion of the catheter; and FIG. 6 is an enlarged cross-sectional view of the balloon catheter with fibers reinforcement fused in the walls of the catheter tubing.

DETAILED DESCRIPTION OF THE DRAWINGS

The best mode and preferred embodiment of the invention is disclosed by FIGS. 1 through 4 and 6 and illustrates a catheter 10 made of polyurethane and formed with a blow molded thinned portion 12 in the wall of the catheter tubing 11. The portion 12 is thinned so that when a fluid 14 is introduced under pressure into the tubular catheter, a balloon 16 will form in the thinned portion 12. The tubular catheter 10 may be formed by sealing a distal end 15 of a polyurethane extruded tubing and placing the tubing within a mold lined with a reinforcement netting structure 110, preferably of woven glass fibers. The mold M partially shown in phantom in FIG. 5 includes a wider portion 50 adjacent the sealed distal portion 15 of the tube where the reinforcement lining structure is omitted. The tubing is heated and blown outward to fuse with the reinforcement glass fiber structure, as well as to create a thinned out portion 12 of a size and position corresponding to that of the wider portion of the mold described above. The balloon portion thus is thinned with respect to the other portions of the tube and has an exact shape and size. Alternately, the balloon is formed in a thin section of the polyurethane tubing by stretching the polyurethane tubing in the long axis of the tubing while molten.

The catheter 10 also includes an inflation lumen 19 open at its proximal end 17.

In use on a patient the thinned balloon portion 12 is stretched out by insertion of a wire guide 20 through lumen 19 so that the catheter 10 can be introduced through an area of obstruction 100 in the blood vessel 102. When the thinned portion 12 of the catheter 10 is within obstruction 100, the guide wire 20 is removed and a syringe 22 is attached to an adapter 24 on the proximal end 17 of the tube to inflate the balloon. A non-compressible medically compatible liquid 14 is generally used as the fluid for this purpose. The catheter 10 is placed in an open vessel 102 at surgery or can be introduced into an artery through a needle. The catheter can contain radio opaque markings so that it can be positioned in areas of narrowing by use of X-ray imaging. The balloon 16 can also be inflated with radio opaque material.

A guide wire 20 is longer than the catheter tubing and when placed in the catheter 10 locks into the adapter 24. This insures that the thinned portion 12 of the catheter 10 is stretched to proper length in the longitudinal direction during the catheter introduction. The guide wire 20 serves to stretch and stiffen the tubing and acts as a radio opaque guide wire. The guide wire 20 can be mitred as shown by the numerals 27 to measure distances in the X-ray image by notching the wire 20 at set intervals. The tubing can also be banded with steel collars 32 as shown in FIG. 6 at the beginning and ending of the thinned portion 12 to indicate the length of the balloon.

After the catheter 10 has been placed in a correct position in obstructed area 100, the guide wire 20 is removed; a syringe 22 is connected to adaptor 24 and the balloon 16 is expanded with fluid.

In an alternate embodiment, shown in FIG. 5, braided shell wire reinforcement is used rather than the preferred embodiment of woven glass or fine fibers and the braids are placed at the beginning and end of the thinned portion of the balloon section, but not at the center. This reinforces the tubing onto the thinned portion 12, but not in the center of the thinned portion. In this regard, La Place's law states that the tension on a wall is proportional to both the pressure within the catheter 10 and the diameter thereof.

While the balloon 16 is without reinforcement, it is also constrained by the occlusion 100 and will not expand to the point where the tensile strength of the balloon 12 equals the tension thereon. Thus, balloon 12 will not rupture.

It should be understood that the examples set forth are not meant to limit the invention in any manner nor is the invention limited to any one embodiment described herein. On the contrary, uses intended to cover all alternatives, modifications and equivalents may be included within the spirit and scope of the appended claims.

What is claimed is:

1. An expandable balloon catheter comprising an elongate flexible cylindrical tube having proximal and distal ends, said tube defining an inflation lumen means within said tube, said lumen means being sealed at said distal end and open at said proximal end of said tube, said tube including a unitary balloon portion adjacent to and spaced apart from said distal end, said balloon portion of said tube being thinner than the remaining portion of said tube, and a woven reinforcing structure combined with said remaining portion of said tube, said woven reinforcing structure overlapping opposite ends of said balloon portion to reinforce the remaining portion of the tube onto the balloon portion.

2. The apparatus of claim 1, wherein said tube is formed from polyurethane.

3. The apparatus of claim 1, wherein a connection adaptor is fixed to the proximal end of said tube.

4. The apparatus of claim 1, wherein said woven reinforcing structure is a netting of glass fibers within said tube.

5. The apparatus of claim 1, wherein said woven reinforcing structure is a braided wire.

6. The apparatus of claim 1, including metal banding surrounding said tube on opposite ends of said balloon portion of said tube to indicate the length of the balloon portion.

7. A unitary blow-molded expandable balloon catheter comprising an elongated hollow tube with an external diameter no greater than the internal diameter of a human blood vessel into which it is to be inserted, said tube provided with an inflation lumer, a sealed distal end for insertion into said human blood vessel, and an open proximal end for connection to inflation means and tensioning means, said tube defining an inflatable balloon comprising a unitary portion of said tube adjacent to and spaced apart from said distal end, said balloon being of predetermined length and of lesser tube wall thickness than that of said tube between said balloon and said proximal end and between said balloon and said distal end, and said elongated hollow tube between said balloon and said proximal end and between said balloon and said distal end being composed of an elastomeric polymer containing a woven fibrous reinforcement material to reinforce these portions of the tube onto the balloon portion.

* * * * *